United States Patent [19]
Jönsson et al.

[11] Patent Number: 5,972,223
[45] Date of Patent: Oct. 26, 1999

[54] METHOD AND APPARATUS FOR THE CENTRAL PREPARATION AND DISTRIBUTION OF SALT CONCENTRATES

[75] Inventors: Lennart Jönsson, Furulund; Birger Hallberg, Bjärred; Sven Jönsson, Staffanstorp; Stefan Knutsson, Bjärred; Lennart Olsson, Lund, all of Sweden

[73] Assignee: Gambro AB, Sweden

[21] Appl. No.: 08/529,014

[22] Filed: Sep. 15, 1995

[30] Foreign Application Priority Data

Sep. 20, 1994 [SE] Sweden .................................. 9403142

[51] Int. Cl.⁶ .......................... B01D 61/26; B01D 61/28
[52] U.S. Cl. .............................. 210/647; 210/85; 210/90; 210/97; 210/194; 210/195.1; 210/321.71; 210/417; 210/456; 210/636; 210/645; 210/646; 210/805; 137/88; 366/150.1; 422/1; 422/38
[58] Field of Search ...................... 210/645, 646, 210/647, 85, 90, 97, 117, 195.1, 195.2, 194, 321.71, 321.65, 417, 805, 456, 636; 137/88; 366/150.1; 422/1, 38

[56] References Cited

U.S. PATENT DOCUMENTS

| | | | |
|---|---|---|---|
| 3,352,779 | 11/1967 | Austin et al. | 210/321.71 |
| 4,085,046 | 4/1978 | Saporito, Jr. | 210/321.71 |
| 4,107,039 | 8/1978 | Lindsay, Jr. et al. | 210/321.65 |
| 4,784,495 | 11/1988 | Jonsson et al. | 137/88 |
| 5,015,389 | 5/1991 | Portillo, Jr. | 210/646 |
| 5,091,094 | 2/1992 | Veech | 210/647 |
| 5,295,505 | 3/1994 | Polaschegg et al. | 210/321.71 |
| 5,616,248 | 4/1997 | Schal | 210/647 |

FOREIGN PATENT DOCUMENTS

| | | |
|---|---|---|
| 0 058 303 A1 | 5/1982 | European Pat. Off. . |
| 0 058 304 A1 | 8/1982 | European Pat. Off. . |
| 0 208 090 A1 | 1/1987 | European Pat. Off. . |
| 0 209 607 A1 | 1/1987 | European Pat. Off. . |
| 0 278 100 A2 | 8/1988 | European Pat. Off. . |
| 0 439 793 A2 | 8/1991 | European Pat. Off. . |
| 0 443 324 A1 | 8/1991 | European Pat. Off. . |
| 0 458 041 A1 | 11/1991 | European Pat. Off. . |
| 0 401 130 B1 | 11/1993 | European Pat. Off. . |
| 0 605 395 A1 | 7/1994 | European Pat. Off. . |
| 34 43 911 A1 | 6/1986 | Germany . |
| 42 03 905 C2 | 8/1993 | Germany . |

*Primary Examiner*—John Kim
*Attorney, Agent, or Firm*—Lerner, David, Littenberg, Krumholz & Mentlik, LLP

[57] ABSTRACT

Methods for the central preparation and distribution of a concentrate to a plurality of medical treatment devices are disclosed comprising supplying a stream of substantially only water to a central container which includes a single salt composition at least partially in solid form, producing a substantially saturated solution of the salt composition in the central container, and distributing the salt solution to a distribution conduit which includes a plurality of concentrate connectors whereby the salt solution can be distributed to the plurality of medical treatment devices. Methods for disinfecting this apparatus, the apparatus itself, and containers for use in the apparatus are also disclosed.

43 Claims, 4 Drawing Sheets

Fig.5
Fig.6
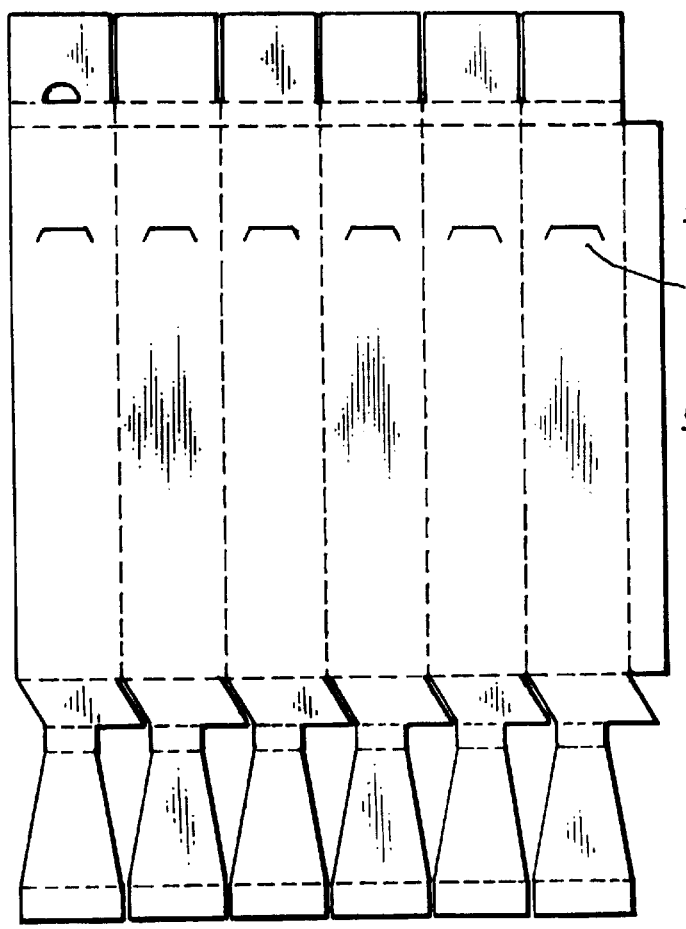
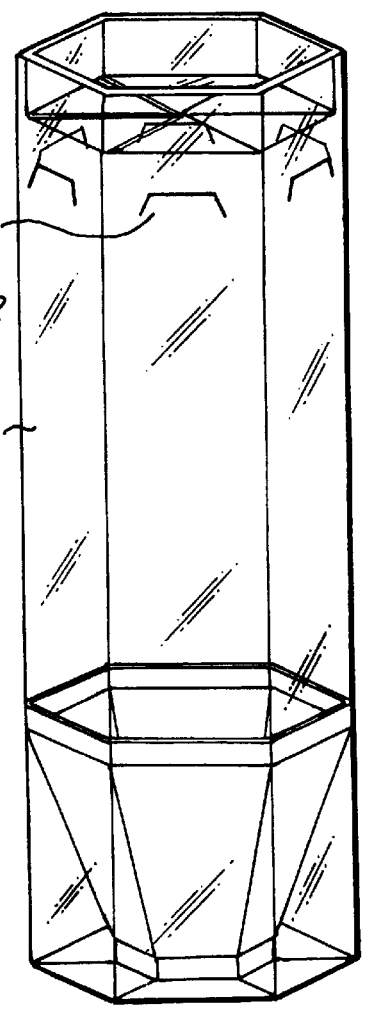

METHOD AND APPARATUS FOR THE CENTRAL PREPARATION AND DISTRIBUTION OF SALT CONCENTRATES

FIELD OF THE INVENTION

The present invention relates to methods and apparatus for preparing solutions for medical purposes. More particularly, the present invention relates to such methods and apparatus for preparing dialysis solutions and/or replacement solutions for use in hemodialysis, hemodiafiltration or hemofiltration, as well as other liquids for medical use, such as infusion solutions, peritoneal dialysis solutions, nutritional solutions, and the like. Still more particularly, the invention relates to methods for disinfecting such apparatus and vessels intended for use in such apparatus.

BACKGROUND OF THE INVENTION

In dialysis clinics for hemodialysis, large numbers of patients are treated simultaneously. Each patient is thus connected to a dialysis machine, a so-called monitor, which prepares the dialysis solution and administers the solution to a dialyzer, which is connected to the patient.

In monitors which are presently in use, such as the GAMBRO AK-100 monitor, preparation of the dialysis solution normally takes place by mixing two dialysis concentrates to produce a desired composition and concentration.

The dialysis concentrate can be an A-concentrate, which consists of acetic acid, sodium chloride, potassium chloride, calcium chloride and magnesium chloride, and a B-concentrate, consisting of bicarbonate. Reference is made to European Patent No. B1-0 278 100 for further details thereof.

These concentrates are diluted with water, which is normally obtained from a particular water outlet at each treatment location. The water must be specially treated so that it contains as few impurities as possible, and is normally prepared by the so-called RO (reverse osmosis) process. Such a process is described, for example, in European Patent Nos. B1-0 058 303 and BI-0 058 304.

The water is usually purified at a central location, and is conducted to each patient location in a particular conduit system which is constructed with the intention of reducing the possibilities of bacterial contamination. Furthermore, the conduit system is regularly disinfected by feeding warm water, at a temperature above 90° C., through the system.

German Patent No. A1-34 43 911 describes a method and an apparatus for the batchwise preparation of a dialysis solution consisting of common salt, magnesium, calcium, potassium and glucose by mixing with so-called "zero-conductivity water," i.e., purified water, in a large tank. The thus-prepared dialysis solution is then drained into containers of about 10 liters each, and placed at the dialysis clinic's disposal to form the above-mentioned A-concentrate after the addition of acid (which can take place in the monitor itself). The disadvantage with this process is that heavy concentrate-containing containers must be physically handled personnel and transported or carried to each patient location.

German Patent No. C2-42 03 905 describes the distribution of a centrally prepared dialysis solution by means of a conduit system. The disadvantage with such central distribution of dialysis solution is that the dialysis solution is a very good nutritional medium for many bacteria. According to German Patent No. C2-42 03 905, a sterile filter is employed, though this can become quite expensive. Furthermore, very effective disinfection of the conduit system is required. The conduits must first be rinsed clean to remove the dialysis solution, after which hot water or other disinfecting agents are circulated through the conduits.

SUMMARY OF THE INVENTION

One object of the present invention is to propose a practical and useful method and apparatus for centrally preparing solutions or concentrates intended for dialysis or similar medical purposes.

A saturated concentrate solution of sodium chloride, common salt, is a very poor nutritional medium for bacteria, and only a small number of bacteria are known which can survive in such an environment, i.e., so-called halo bacteria.

In addition, a saturated common salt solution may be heated to high temperatures without its properties or solubility being altered.

It has also been shown to be possible to continuously prepare a saturated common salt solution starting from a large quantity of common salt in powder form by means of passing water through the quantity of powder. If the grain size of the common salt crystals lies within a predetermined range, no formation of lumps of common salt occurs even with very large quantities of salt, something which otherwise could be expected. (See European Patent No. B1-0 278 100).

In accordance with the present invention, these objects have now been realized, and the characteristics discussed above have now been utilized by the invention of a method for the central preparation and distribution of a concentrate to a plurality of medical treatment devices comprising supplying a liquid stream comprising substantially only water to a central container including substantially only a single salt composition at least partially in solid form therein, producing a substantially saturated solution of said salt composition in said central container, and distributing said salt solution to a distribution conduct, the distribution conduct including a plurality of concentrate connectors whereby the salt solution can be distributed to the plurality of medical treatment devices.

In accordance with one embodiment of the method of the present invention, the method includes preparing a medical treatment solution from the salt solution in each of the plurality of medical treatment devices. Preferably, the medical treatment solutions include dialysis solutions and replacement solutions for hemodialysis, hemofiltration and hemodiafiltration.

In accordance with another embodiment of the method of the present invention, the method includes heating the liquid stream or the substantially saturated solution of the salt composition to an elevated temperature whereby the salt solution is distributed to the distribution conduit at that elevated temperature.

In accordance with another embodiment of the method of the present invention, the method includes adding a separate substance to the salt solution, preferably acetic acid.

In accordance with one embodiment of the method of the present invention, the medical treatment solution comprises a dialysis solution and the plurality of medical treatment devices comprises a plurality of dialysis machines, and the method includes diluting the substantially saturated salt solution and adding carbon dioxide gas to the substantially saturated salt solution prior to distributing the salt solution to the distribution conduit.

In accordance with another embodiment of the method of the present invention, the method includes distributing the salt solution to the distribution conduit at an elevated pressure.

In accordance with another aspect of the present invention, a method of disinfecting an apparatus for the central preparation and distribution of a concentrate to a plurality of medical treatment devices has been devised, comprising a central concentrate container for preparation of a substantially saturated solution of substantially only a single salt composition and distribution means for distributing the salt solution to a plurality of concentrate connectors whereby the salt solution can be distributed to the plurality of medical treatment devices, the method comprising circulating the salt solution in a recirculation circuit including the distribution means and heating the salt solution to an elevated temperature in order to disinfect the recirculation circuit thereby. Preferably, the method includes recirculating the salt solution in the recirculation circuit at an elevated pressure.

In accordance with the apparatus of the present invention, apparatus for the central preparation and distribution of a concentrate to a plurality of medical treatment devices has been devised, comprising central concentrate preparation means for preparing a substantially saturated solution of substantially only a single salt solution from the salt at least partially in solid form and a supply of water, inlet means for supplying the water to the central concentrate preparation means, and conduit means for supplying the salt solution to a distribution conduit for distribution to the plurality of medical treatment devices. In a preferred embodiment, the central concentrate preparation means comprises at least one container for the salt at least partially in solid form.

In accordance with another embodiment of the apparatus of the present invention, the plurality of medical treatment devices comprises a plurality of dialysis machines, and preferably the at least one container includes salt in an amount of at least about 10 kg, preferably greater than about 20 kg, and more preferably greater than about 40 kg.

In accordance with another embodiment of the apparatus of the present invention, the salt comprises sodium chloride in a particulate form, and preferably the particles of sodium chloride have a particle size of between about 50 and 200 $\mu$m.

In accordance with another embodiment of the apparatus of the present invention, the central concentrate preparation means includes a water tank, and the inlet means includes a water supply conduit for supplying the water from the water tank to at least one container for the salt, return conduit means for returning the salt solution to the central concentration means, and pump means for pumping the salt solution to the conduit means. In a preferred embodiment, the apparatus includes pressure means for measuring the pressure downstream of the at least one container and upstream of the pump means. In another embodiment, the apparatus includes concentrate meter means for measuring the concentration of the salt in the salt solution upstream of the conduit means, and valve means for selectively diverting the salt solution for disposal based upon the reading of the concentrate meter means.

In accordance with another embodiment of the apparatus of the present invention, the apparatus includes metering means for metering an additional substance into the water or the substantially saturated salt solution in the central concentrate preparation means. In a preferred embodiment, the additional substance is an acid, preferably acetic acid, or carbon dioxide.

In accordance with another aspect of the present invention, a container is provided for use in an apparatus for the central preparation and distribution of a concentrate to a plurality of medical treatment devices comprising central concentrate preparation means for preparing a substantially saturated salt solution of substantially only a single salt composition from the salt at least partially in solid form and a supply of water, inlet means for supplying the water to the central concentrate preparation means, and conduit means for supplying the salt solution to the distribution conduit for distribution to the plurality of medical treatment devices, the container for incorporation into the central concentrate preparation means including sodium chloride in particle form in a quantity of at least about 10 kg, the container including inlet means for the water and outlet means for the substantially saturated salt solution, the inlet means including first connecting means and the outlet means including second connecting means, the first and second connecting means being compatible with each other. In a preferred embodiment, the container includes more than about 20 kg of the sodium chloride in particulate form, and more preferably more than about 40 kg of the sodium chloride in particulate form. In another preferred embodiment, the first connecting means comprises male connecting means and the second connecting means comprises female connecting means.

In accordance with the present invention, there is thus provided a method for centrally preparing and distributing a concentrate of substantially only one salt in water for preparation of a medical solution starting from the concentrate. This includes medical solutions such as dialysis solutions and/or replacement solutions for hemodialysis, hemofiltration or hemodiafiltration. In accordance with this invention, the method includes supplying primarily water to a container containing the salt at least partially in solid form, removing a substantially saturated concentrate of the salt in water from the container, and distributing the concentrate to a distribution conduit and concentrate connectors arranged thereon, for preparation of the medical solution. The concentrate and/or water may be heated to a high temperature for distribution of the concentrate at said temperature to the distribution conduit. It is also possible to add a substance such as acetic acid to the concentrate or the water.

In an alternative embodiment of this invention, the concentrate is diluted to a suitable concentration for the dialysis solution, and carbon dioxide gas may be added before distribution to the distribution conduit.

In accordance with the present invention, there is also provided apparatus for carrying out the above-mentioned method for centrally preparing and distributing a concentrate of substantially only one salt in water, for preparing a medical solution starting from the concentrate, for example dialysis solution and/or replacement solution for hemodialysis, hemofiltration or hemodiafiltration. This apparatus comprises a concentrate generator provided with an inlet for purified water and at least one distribution conduit for distribution of the concentrate to at least one concentrate connector, and further comprising at least one container for the salt which is at least partially in solid form, a conduit for supplying primarily water to the container to form a substantially saturated concentrate of the salt in water in the container by partially dissolving the salt in the water, and a conduit for feeding the concentrate to the distribution conduit. It is preferable that the container contain the salt in a quantity of at least 10 kg, preferably more than 20 kg, and most preferably more than 40 kg. Preferably, the salt is sodium chloride in particle form, which particles have a size between about 50 and 200 $\mu$m.

In a preferred embodiment of the apparatus of the present invention, the concentrate generator includes a water tank to which primarily water is fed through an inlet, a conduit for supplying water from the water tank to one of the containers, a return conduit for returning substantially saturated concentrate form the container to the concentrate generator, and a pump for feeding the concentrate solution to the distribution conduit. Furthermore, a pressure meter is preferably arranged in association with the inlet to the pump to detect a pressure downstream of the container, a concentration meter is included for measuring the concentration of the salt in the concentrate before it is fed to the distribution conduit, and a valve for directing the concentrate to a drain should an error arise.

The present invention also relates to a method for disinfecting the above-identified apparatus for the central preparation and distribution of a concentrate of substantially one salt in water, and consisting of a concentrate generator and at least one distribution conduit for distribution of the concentrate to at least one concentrate connector, wherein the concentrate is recirculated in a recirculation circuit comprising at least the distribution conduit, and in which the concentrate is heated to a high temperature, and preferably at an overpressure, to attain disinfection of the recirculation circuit.

Finally, the present invention also comprises a container intended for use in the above-mentioned apparatus and containing sodium chloride in particle form in a quantity of at least 10 kg, preferably more than 20 kg, and most preferably more than 40 kg, and being provided with an inlet for water and an outlet for concentrate, which inlet and outlets preferably have different connecting means, for example of the male and female type, respectively.

BRIEF DESCRIPTION OF THE DRAWINGS

The present invention will be described in the following in greater detail by way of reference to preferred embodiments of the invention and with reference to the attached drawings, in which:

FIG. 5 is a plan view of a blank which is intended to form the container according to FIG. 4; and FIG. 6 is a front, perspective view of a container of the present invention without the inner bags.

DETAILED DESCRIPTION

Figure 1:
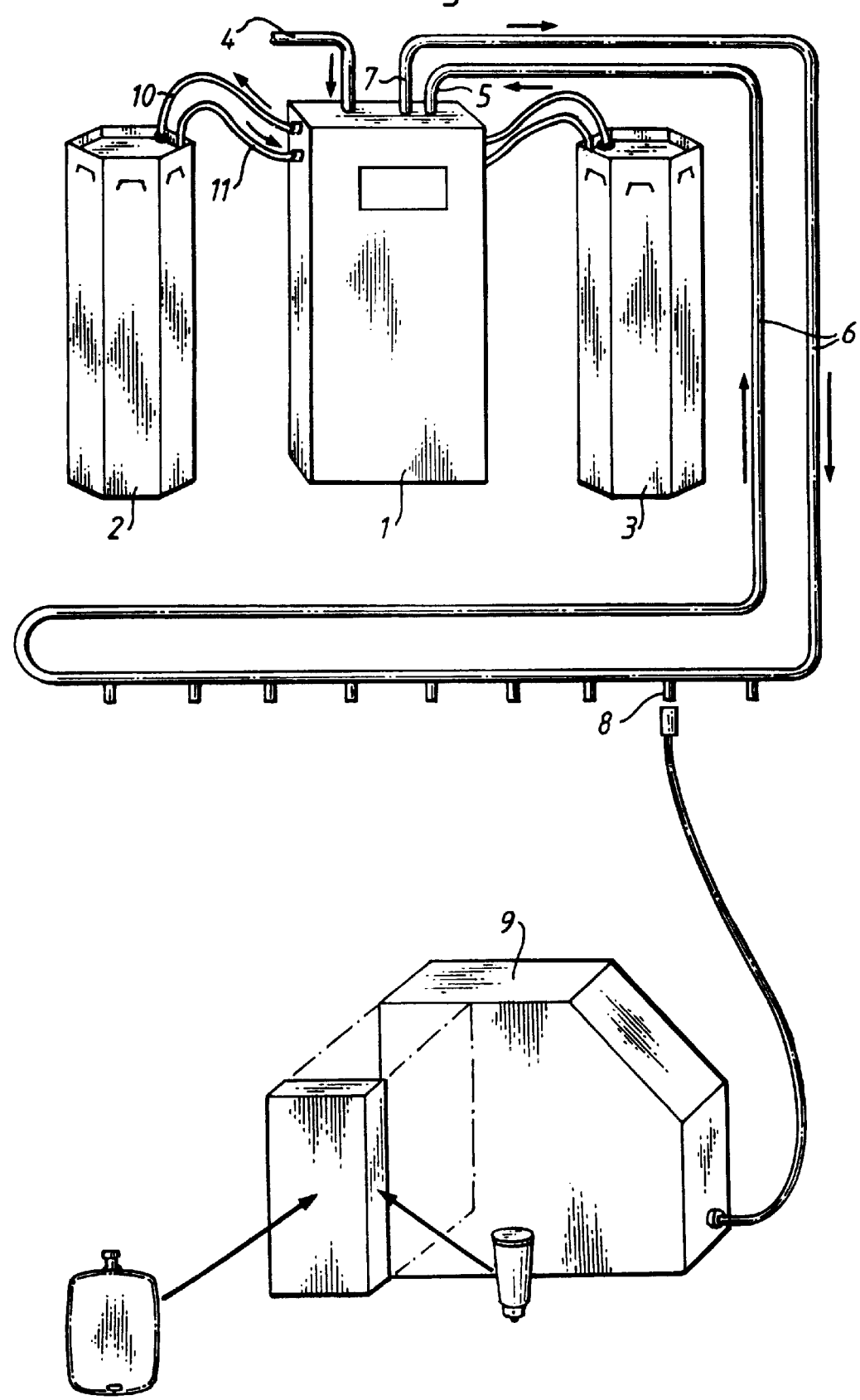
FIG. 1 is a schematic diagrammatic representation, partially in perspective, of one embodiment of the present invention.

Referring to the Figures, in which like reference numerals refer to like elements thereof, FIG. 1 shows a first embodiment of the present invention. The apparatus according to this invention comprises a concentrate generator 1 with two salt containers, 2 and 3, for containing, e.g., sodium chloride (NaCl) in powder form connected thereto. In addition, a water inlet 4 and a concentrate outlet 5 (preferably for substantially saturated concentrated sodium chloride solution) are provided. The invention can be used with other salts or electrolytes, but for the sake of simplicity it will be described herein when used with NaCl, or common salt.

In addition, a distribution conduit 6 for the concentrate is provided which is preferably arranged in the form of a closed loop connected between the concentrate outlet 5 and return inlet 7 on the concentrate generator 1.

The distribution conduit 6 is provided with a plurality of concentrate connectors 8 to which one or more dialysis machines 9 for preparing and administering a dialysis solution are connected. In principle, any type of dialysis machine can be connected, though the dialysis machine should, of course, be adapted, and provided with an inlet, for substantially saturated NaCl solution.

By way of example, one such dialysis machine is GAMBRO AK-100, the construction of which is apparent from, for example, European Patent No. B1-0 278 100. This dialysis machine prepares a ready-to-use dialysis solution starting out from a dry powder (such as bicarbonate powder) and other concentrate with predetermined compositions. A further example is apparent from European Patent No. A1-0 443 324. In the dialysis machine according to any one of these patent documents, the particular preparation of NaCl concentrate is replaced by the connection to the concentrate connector 8 according to the present invention.

Each salt container, 2 and 3, is connected to the concentrate generator 1 by means of two conduits, 10 and 11. Conduit 10 supplies water to the upper region of the container, and conduit 11 returns saturated concentrate of NaCl solution from the lower region of the container. The concentrate is thereafter fed to the distribution conduit 6 through outlet 5, which is shown in greater detail in FIG. 2. Of course, such feeding can take place in the lower region of the container, and removal in the upper region, if so desired. Other variations are also possible.

Figure 2:
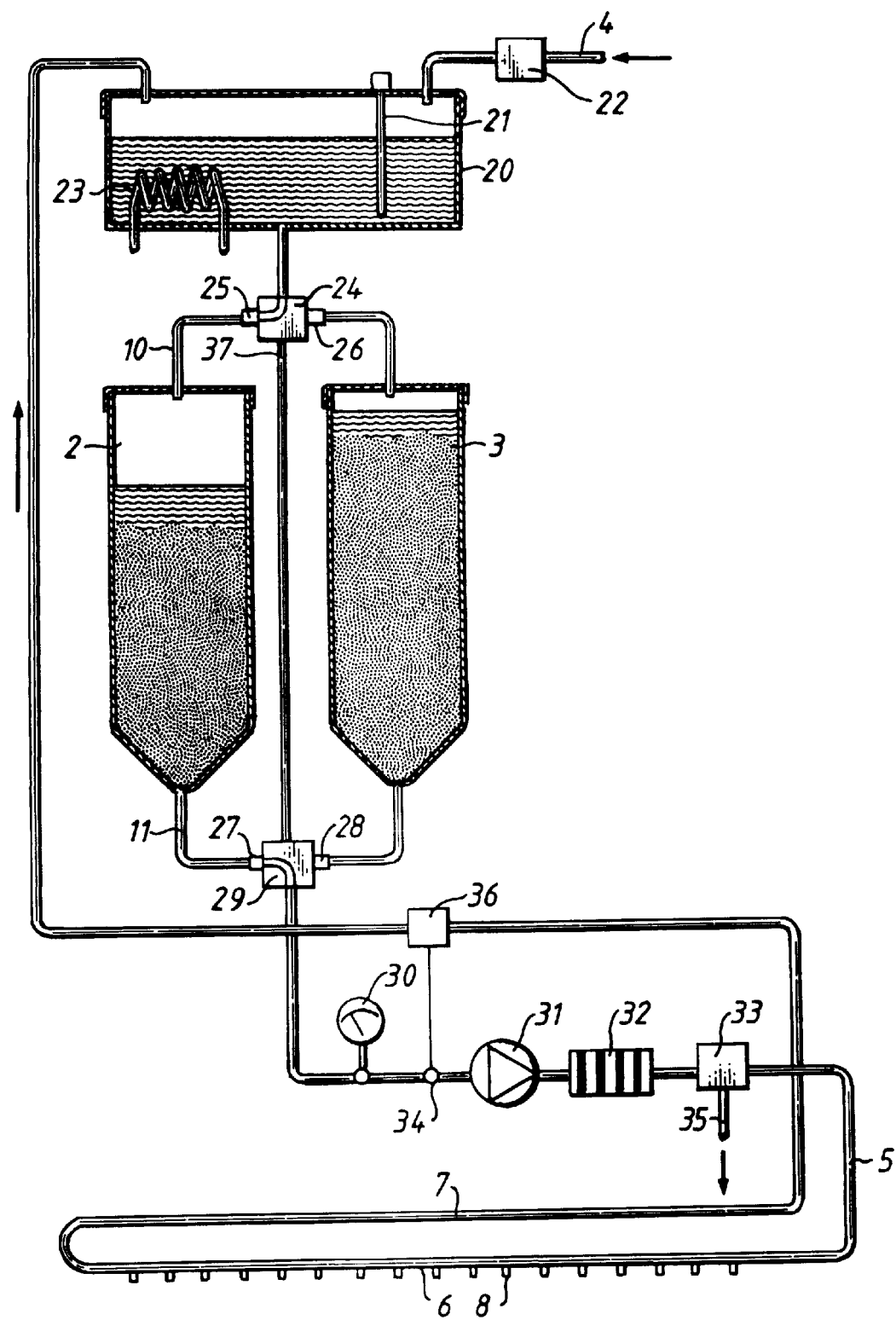
FIG. 2 is a more detailed schematic diagrammatic representation of another embodiment of the present invention.

The principle behind the arrangement according to the invention is shown in more detail in FIG. 2. As is apparent in FIG. 2, water enters the concentrate generator 1 through inlet 4 to a water tank 20. The water level in the tank 20 is controlled by a level sensor 21 which controls an inlet valve 22. The tank 20 can include a heat source 23 for heating the water and/or for regulating the water temperature by means of a temperature sensor.

The incoming water should be purified in a suitable manner, for example using filters of various types (ion exchange filters) and reverse-osmosis processes. The water is thus free from impurities, such as salts, particles and bacteria.

The water is conducted from the tank 20 to a first valve 24 and from there to a water outlet 25 for connection to a container 2 with NaCl powder through conduit 10. Saturated NaCl solution is returned form the container 2 through conduit 11 to a concentrate inlet 27, which leads to a second valve 29. A second container 3 is connected between a water outlet 26 associated with the first valve 24 and a concentrate inlet 28 which is connected to the second valve 29. It will be apparent that by switching the valves 24 and 29, the first container 2 or the second container 3 can alternatively be connected to the concentrate generator 1. It will further be apparent that more than two containers can be connected in parallel if so desired by arranging more water outlets and concentrate inlets to the valves 24 and 29, respectively. While one of these containers is connected, the other container can be exchanged and prepared for use, in which manner continuous supply can be assured.

The concentrate flows from the second valve 29 through a pressure meter 30, a pump 31, a conductivity meter 32 and a third valve 33 to the concentrate outlet 5 for further transport to the distribution conduit 6 and the concentrate connectors 8, and then back to the return inlet 7.

From the return inlet 7, the returned concentrate is fed through a fourth valve 36 back to a mixing point 34 upstream of the pump 31 for recirculation in the distribution conduit 6. The third valve 33 is arranged to direct the concentrate to a drain 35 if the conductivity meter 32 provides a value which does not lie within a predetermined range substantially corresponding to concentrated sodium chloride solution. It will be apparent that other types of meters other than conductivity meters can be used, such as ion-selective meters, etc.

The above-mentioned meters 30 and 32, and devices 33, 34 and 36 are not completely necessary for the system (with the possible exception of the pump 31), but the use of these devices does improve the safety thereof. It is to be noted that corresponding safety features are normally provided in the dialysis machine.

It should be mentioned that it is not necessary to recirculate the saturated concentrate, but instead the return inlet 7 and the recirculation can be omitted in certain applications. Furthermore, it is not always necessary to have the tank 20 for water. The water can instead thus be fed directly to the containers, 2 and 3. The water tank 20 can also be smaller in size and in principle may only contain the heating source 23 for on-line heating of the incoming water. Thus, the term "water tank" is meant to include all different sizes from, in principle, merely a widening of a conduit to rather large storage tanks.

Figure 3:
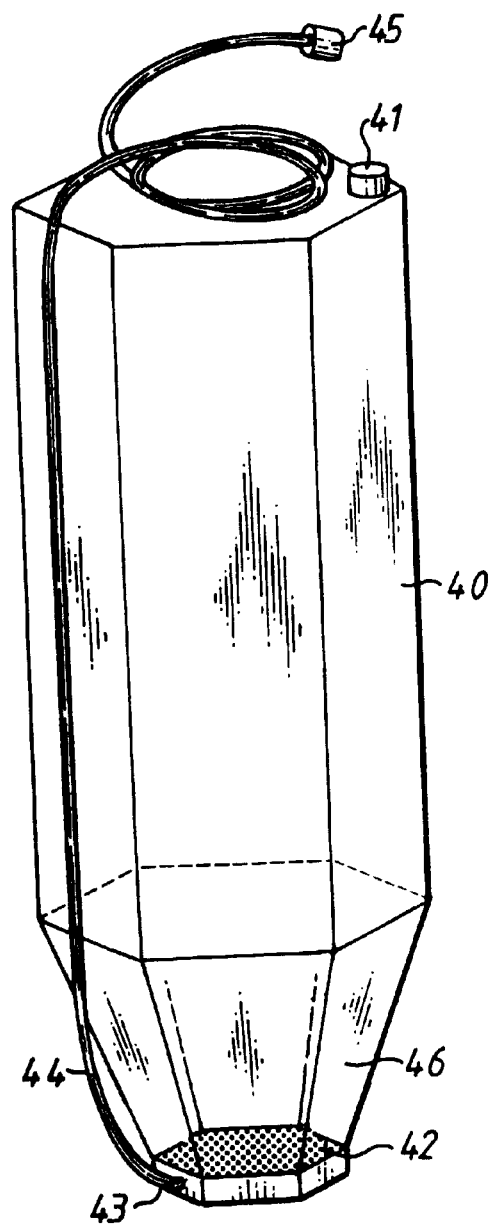
FIG. 3 is a schematic, partially perspective view of an inner bag intended for use according to the present invention.

The containers 2 and 3 contain sodium chloride in powder form in a large bag or sack. One embodiment of the bag is shown in more detail in FIG. 3, and consists of a six-sided inner bag 40 made from polyethylene or polypropylene, or similar such materials. The inner bag can be totally or partially stiff or self-supporting so that it adopts the shown shape, or alternatively, it can be flexible.

An inlet 41 for water for connection to the conduit 10 is provided at the upper end of the bag. In addition, particle filter 42 and an outlet 43 in the form of a tube 44 are provided at the lower end of the bag, the tube opening out into a connector 45 which forms the outlet for saturated concentrate. The tube 44 and the connector 45 correspond to the conduit 11 in FIG. 1.

The connector 45 and the inlet 41 are differently shaped, such as male and female connectors respectively, to avoid incorrect coupling. Furthermore, the connector 45 can be directly connected to the inlet 41 to seal the bag during transport or when the bag is not in use.

It is also possible to connect several bags in series to extend the operating time. Since water is supplied to the first of the series-connected bags, the powder in the first bag will be consumed first, and thereafter the powder in the next bag will be consumed. Since concentrate is removed from the last bag of the series-connected bags, the powder in all of the series-connected bags will be consumed successively.

At least the lower region 46 of the bag is conical, which facilitates the utilization of all the sodium chloride in the bag.

Figure 4:
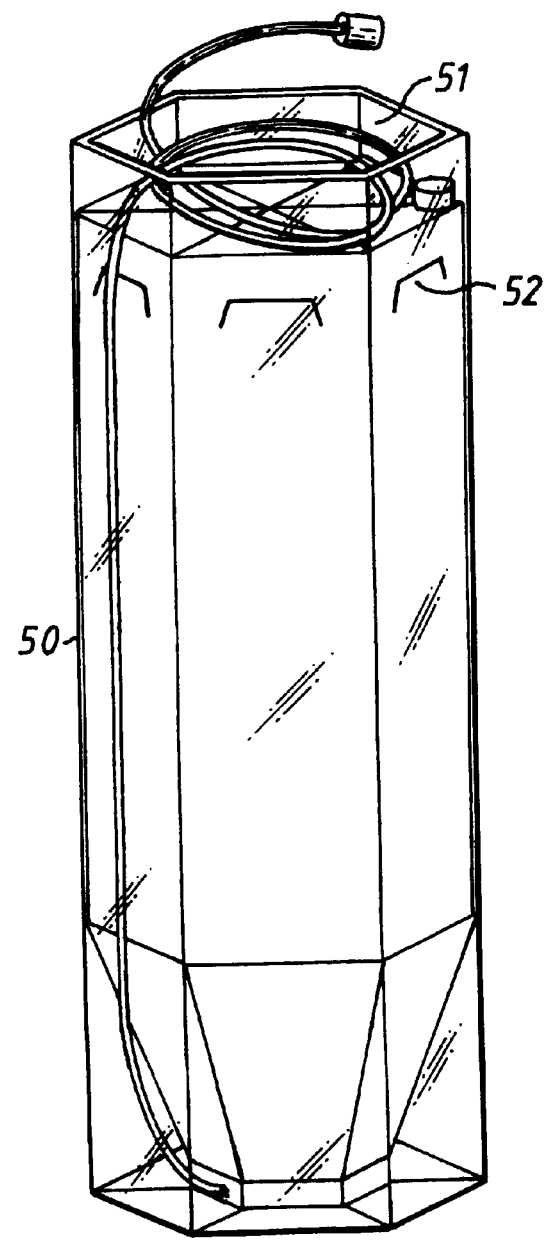
FIG. 4 is a front, perspective view of a container provided with an inner bag for use in the embodiment according to FIG. 3.

The inner bag is housed in a protective casing 50, as shown in FIG. 4. The casing is manufactured from cardboard or hard plastic, or a similar such material. The casing 50 is shown in FIG. 4 with the inner bag arranged therein. As is apparent from FIG. 4, an upper chamber 51 is created above the inner bag in which the tube 44 and the connector 45 can be accommodated during transport.

The casing can be made from a blank which is shown in detail in a flat condition in FIG. 5,, and in an erect condition in FIG. 5. Suitably, handles 52 are stamped out in the side. Alternatively, carrying means such as straps can be provided to facilitate transport thereof.

The inner bag 40 is filled by the manufacturer with sodium chloride in powder form and is then transported to the user, who may be a dialysis clinic, etc. The shape of the casing is selected so that it can be easily transported by conventional means, for example on load pallets of standard 800×1200 mm size.

It is already known per se to use common salt (NaCl) in cartridges, and to allow water to flow through the cartridge and dissolve the common salt online as is required. In the above-mentioned European Patent No. B1-0 278 100, a cartridge is described containing about 1000 g of common salt, where it has been determined that a particle size between about 50 $\mu$m and 200 $\mu$m is suitable.

It has surprisingly been shown that such a cartridge can be made very large without the risk of lump formation of the common salt during operation with the granule sizes which are mentioned above. According to the present invention, this discovery is used to produce "cartridges" on the order of tens of kilograms in weight for central preparation of NaCl concentrate "on-line," whereby the common salt is dissolved during use. In this manner, batchwise preparation of the NaCl concentrate in large mixing vessels having a volume of tens of cubic meters is avoided.

By using common salt bags of this size, transport of large quantities of water which was previously required is avoided, thereby leading to large savings. Furthermore, large quantities of salt can be transported in one and same bag and prepared online in a central system according to the present invention. No reloading is thus necessary, but instead the container can be used in the form in which it arrives at the clinic.

Preparation of the concentrate takes place by supplying water, preferably purified water, to the common salt in powder form in the container or the inner bag. Water is supplied in such a quantity that the water level in the bag is above or level with the level of the common salt in the bag, which need not be all the way up to the upper end of the bag.

When the water is supplied to the powder, a mass of common salt particles is created which can move around each other in a manner similar to small stones in water. The particles are continuously dissolved so that the water becomes saturated with common salt. Thereafter, no further continued dissolving takes place. Instead, the saturated common salt solution and the common salt particles are in equilibrium.

When concentrate is removed through conduit 11, the same quantity of water is supplied via the conduit 10 and the common salt is dissolved anew, so that the incoming water becomes saturated with common salt. Thus, the common salt particles are continuously consumed during withdrawal of concentrate. In between, no consumption of common salt particles takes place since the solution is saturated. Agglomeration is avoided, as mentioned above, by selection of the particle size of the common salt particles. As soon as the NaCl powder is completely wetted, a mass or slurry of common salt powder and water is formed which exhibits no tendency to lump together but instead remains as a shapeless mass, with the common salt powder in solid form and water substantially saturated with dissolved common salt.

In order to take full advantage of the invention, it is suitable that the inner bag be so big that it is advantageous from a transportation point of view. Accordingly, it is preferred that the bag contain at least about 10 kg of salt, and preferably more than about 20 kg of salt. A preferred size is about 40 kg of salt, above which size the bag can become difficult to handle. Bags of around 65 kg and up to about 100 kg can still be possible.

As mentioned above, saturated NaCl solution is a very poor growth medium for bacteria. Despite this fact, the distribution conduits 6 and the concentrate connectors 8 must still be disinfected at regular intervals.

For this purpose, another positive property of NaCl solution, namely that the solubiltiy is substantially temperature independent, is exploited. It is therefore possible to heat saturated NaCl solution to a high temperature suitable for disinfecting without the risk of precipitation or crystal formation or that the properties of the concentrate be changed. Accordingly, the conduits 6 and the connectors 8 can be disinfected by the concentrate itself without having to first flush them clean of concentrate.

During disinfecting, the fourth valve 36 is first switched to a disinfecting position for recirculation of the concentrate to the water tank 20.

A bypass conduit 37 between the first valve 24 and the second valve 29 bypasses the containers 2 and 3, since the plastic material in the containers otherwise might potentially be damaged by the high temperature, and the time required for the heating up would also be extended. In this manner, the entire concentrate generator, including the water tank 20, is filled with concentrate. Alternatively, the water in the water tank 20 can be used to dilute the concentrate in the conduit 6 so that this solution, which is used for disinfecting, is not totally saturated. As an alternative, only water, or water including only a small portion of salt, can also be so utilized.

The heating source 23 is now activated to gradually heat the concentrate to such a temperature that disinfecting takes place, for example a temperature above about 90° C., preferably abut 98° C., or up to about 105° C., and the circulation is allowed to continue for a suitable period of time, for example at least 30 minutes. Thereafter, the system is allowed to cool and the valves are switched to normal operation.

If the system is closed, even higher temperatures can be used, for example up to about 121° C., at which sterilization is achieved. In this manner, an overpressure of about one atmosphere is attained in the system.

The above-described disinfecting can be executed entirely automatically, for example at night, when the dialysis clinic is not normally in operation.

It is possible to operate the concentrate generator 1 at a continuously high temperature, whereby disinfecting is achieved during operation. For reasons of safety, it can be suitable to maintain this temperature at about 60° C., but it is also possible to use temperatures in the order of just over 90° C. In the latter case, it should be ensured that the connectors to the dialysis machine have safety means so that scalding cannot occur.

As an alternative, or complementary to the particular by-pass conduit 37, the conduit 10 can be disconnected from the container 2 and connected directly to the corresponding concentrate inlet 27 so that the concentrate can flow along this path during disinfecting.

It will be appreciated that disinfecting agents other than saturated common salt concentrate can be used in the system according to the present invention.

It can be suitable to fill the common salt containers 2 and 3 with water at the same time that they are connected to the concentrate generator 1 according to the present invention, i.e., so-called priming. The reasons for this are many, such as the fact that the common salt powder should be moistened before use, and for purposes of flushing out particles which may have lodged in the tubes or the connectors. During this priming step, the third valve 33 is set so that the concentrate is fed to the outlet 35, and the pump 31 pumps water from the tank 20, through the tubes 10 and 11 to the drain. After a short period of time, and when the conductivity meter 32 provides correct measured values, the priming step is discontinued by switching the third valve 33 to its normal position.

Priming of one container can take place while the other container is in use. Necessary valves and conduits for this purpose are not shown in the drawings, though these are evident for a skilled person. Moreover, separate pumps and conductivity cells can be arranged for each container to facilitate simultaneous priming. This also applied to means for emptying the entire concentrate generator.

In FIGS. 1 and 2, two containers 2 and 3 are shown connected in parallel. It will be apparent, however, that the second container can be connected when the first container is empty so that a longer operating time can be achieved, which occurs with valves 24 and 29. An indication that one container is empty is thus obtained by means of the conductivity meter 32. Alternatively, the pressure meter 30 can be used, which indicates a lower pressure as the container is emptied, or visual indication on the NaCl containers can be employed. Further pressure meters can be placed in other positions in the system, for example in outlets 25 and 26, for controlling the filling of each container.

The containers and the system hereof are particularly suitable for preparation of saturated common salt solution for use in hemodialysis, hemofiltration or hemodiafiltration. The other constituents of the dialysis solution are prepared by the monitor, such as bicarbonate solution via a BICART® cartridge, a product of GAMBRO AB, and remaining electrolytes by means of a bag containing such electrolytes in concentrated dissolved form, for example in a concentration of 1:400. These electrolytes can be potassium chloride, calcium chloride, magnesium chloride and possibly glucose. In addition, acetic acid is normally added to adjust the pH value to from about 7.2 to 7.4 in the final dialysis solution.

The composition of the prepared dialysis solution is determined by the dialysis machine. The concentration of the substantially saturated common salt solution is measured by the dialysis machine, and the measured value controls a pump or valve so that the correct quantity of common salt is mixed into the dialysis solution.

Salts other than common salt can also be prepared centrally according to the present invention. One such salt is potassium chloride, which has substantially the same properties as common salt. However, such small quantities of potassium chloride are used in the dialysis solution that the economic benefits of central preparation of potassium chloride concentrate rarely justifies such an investment. Those salts which can be prepared according to this invention should be such salts in which bacteria growth is minimal.

It is possible to prepare several salts in parallel and to distribute these concentrates in separate parallel distribution conduits to the dialysis machine. It is to be noted that with this invention, two parallel distribution conduits are used, one for the concentrate according to the invention, and one for purified water which must also be supplied to the dialysis machine.

It can also be possible to mix two of the ingredients during the course of central preparation of the concentrate according to the present invention. Normally, however, only one salt is included in the concentrate because of the difficulty of dosing the concentrate in the dialysis machine and achieving the correct composition. It can, however, be possible to add an acid to the water tank 20. The acid can be acetic acid, and is used in the dialysis solution to adjust the pH value to avoid precipitation of calcium carbonate and other such impurities.

It is to be noted that the term "water" which is used above can also include water with certain additions, such as acid, etc. In addition, this water can, for example after a disinfection treatment, contain common salt or other electrolytes.

It can also be possible to dilute the common salt concentrate so that it is not saturated when it is fed to the distribution conduit 6. In this manner, the use of two parallel distribution conduits can be avoided, i.e., one for the common salt concentrate and the other for water. Instead, these can be combined in one and the same distribution conduit. In this manner, it is necessary that the solution which is fed to the distribution conduit have the lowest expected concentration for sodium, and a final adjustment of this concentration is made in the dialysis machine according to individual requirements. In this embodiment, carbon dioxide gas can be added to the mixture of water and NaCl, whereby a sufficient quantity of carbon dioxide can dissolve in the mixture so that necessarily low pH values are obtained in the prepared dialysis solution without additional mixing of carbon dioxide or other acids. Since the solubility of carbon dioxide in water is proportional to the pressure, additional quantities of carbon dioxide can be dissolved if the concentrate generator is operated at an overpressure of, for example, about one atmosphere.

During disinfection, it can be suitable to use saturated common salt concentrate to obtain as efficient a disinfection as possible, particularly with regard to the fact that saturated common salt concentrate can be heated to about 107° C. before it boils.

A plurality of distribution conduits 6 which are connected in parallel or in series can be used.

It is preferred to remove the substantially saturated concentrate from the lower portion of the container. It is also possible, however, to remove the concentrate from the upper portion of the container, or from some other intermediate position. It is to be noted that the common salt solution may stratify, particularly when the container includes smaller quantities of common salt in solid form at the end of the container's use. When removing concentrate from the upper portion of the container, the concentrate can thus have a lower concentration than that when it is saturated. Even though common salt has a high solubility, and dissolves quickly in water, under certain operating conditions with high flow velocity of water through the container it may occur that the removed concentrate is not saturated. The expressions "substantially saturated concentrate" and "substantially saturated solution" are intended to include these departures from the concentrated condition, either permanently, for example because of stratification, or constant high flow velocity, or temporarily because of deviations which can exceptionally arise, such as at the end of the use of a container. Normally, monitoring takes place to ensure that the concentrate is sufficiently concentrated or saturated by means of the conductivity meter 32. If concentrate with a concentration which is too low should reach a dialysis machine, the machine will emit an alarm signal to indicate that sufficient final concentration in the dialysis solution cannot be attained.

The invention has been described with reference to a preferred embodiment of the invention. However, it is to be understood that the invention can be modified in many ways by a skilled person reading this description, and the intention is that such modifications which are evident to a skilled person are to be included within the scope of this invention. The various described components can be combined in other ways than those shown in the drawings.

We claim:

1. A method for the central preparation and distribution of a concentrate to a plurality of medical treatment devices for performing a procedure selected from the group consisting of hemodialysis, hemofiltration and hemodiafiltration comprising supplying a liquid stream comprising substantially only water to a central container including substantially only sodium chloride at least partially in solid form therein, producing a substantially saturated solution of said sodium chloride in said central container to form said concentrate, heating said liquid stream or said concentrate during operation of said medical treatment device to an elevated temperature above about 60° C., and distributing said concentrate at said elevated temperature to a distribution conduit, said distribution conduit including a plurality of concentrate connectors for connection to said plurality of medical treatment devices for distribution of said concentrate thereto, whereby simultaneous disinfection is also achieved during operation of said medical treatment device for performing a dialysis treatment.

2. The method of claim 1 including preparing a medical treatment solution from said concentrate in each of said plurality of medical treatment devices.

3. The method of claim 2 wherein said medical treatment solutions are selected from the group consisting of dialysis solutions and replacement solutions for hemodialysis, hemofiltration, and hemodiafiltration.

4. The method of claim 2 including adding a separate substance to said concentrate.

5. The method of claim 4 wherein said separate substance comprises acetic acid.

6. The method of claim 2 wherein said medical treatment solution comprises a dialysis solution and said plurality of medical treatment devices comprises a plurality of dialyzers, and including diluting said substantially saturated sodium chloride solution and adding carbon dioxide gas to said sodium chloride solution prior to said distributing of said salt solution to said distribution conduit.

7. Apparatus for the central preparation and distribution of a concentrate to a plurality of medical treatment devices for performing a procedure selected from the group consisting of hemodialysis, hemofiltration and hemodiafiltration comprising central concentrate preparation means for preparing a substantially saturated solution from substantially only sodium chloride which is at least partially in solid form and a supply of substantially only water, inlet means for supplying said water to said central concentrate preparation means for preparing said concentrate, heating means for heating said concentrate during operation of said medical treatment device to an elevated temperature above about 60° C., and conduit means for supplying said concentrate to a distribution conduit for distribution to said plurality of medical treatment devices, whereby simultaneous disinfection is also achieved during operation of said medical treatment device for performing a dialysis treatment.

8. The apparatus of claim 7 wherein said central concentrate preparation means comprises at least one container for said sodium chloride at least partially in solid form.

9. The apparatus of claim 7 wherein said plurality of medical treatment devices comprises a plurality of dialysis machines.

10. The apparatus of claim 8 wherein said at least one container includes said sodium chloride in an amount of at least about 10 kg.

11. The apparatus of claim 10 wherein said at least one container includes said sodium chloride in an amount of greater than about 20 kg.

12. The apparatus of claim 11 wherein said at least one container includes said sodium chloride in an amount greater than about 40 kg.

13. The apparatus of claim 7 wherein said sodium chloride has a particle size of between about 50 and 200 μm.

14. The apparatus of claim 8 wherein said central concentrate preparation means includes a water tank, and said inlet means includes a water supply conduit for supplying said water from said water tank to said at least one container, return conduit means for returning said concentrate to said central concentrate preparation means, and pump means for feeding said concentrate to said conduit means.

15. The apparatus of claim 14 including pressure means for measuring the pressure downstream of said at least one container and upstream of said pump means.

16. The apparatus of claim 15 including concentrate meter means for measuring the concentration of said sodium chloride in said concentrate upstream of said conduit means, and valve means for selectively diverting said concentrate for disposal based upon said concentration measured by said concentrate meter means.

17. The apparatus of claim 7 including metering means for metering an additional substance into said water or said substantially saturated solution in said central concentrate preparation means.

18. The apparatus of claim 17 wherein said additional substance is selected from the group consisting of an acid and carbon dioxide.

19. The apparatus of claim 18 wherein said acid comprises acetic acid.

20. A container for use in apparatus for the central preparation and distribution of a dialysis concentrate to a plurality of dialysis machines comprising central concentrate preparation means for preparing a substantially saturated salt solution of substantially only a single salt composition from said salt at least partially in solid form and a supply of water, inlet means for supplying said water to said central concentrate preparation means, and conduit means for supplying said salt solution to a distribution conduit for distribution to said plurality of dialysis machines, said container for incorporation into said central concentrate preparation means and including sodium chloride in particle form in a quantity of at least about 10 kg, said container including inlet means for said water and outlet means for said substantially saturated salt solution, said inlet means including first connecting means, and said outlet means including second connecting means, said first and second connecting means being compatible with each others whereby a dialysis fluid can be provided for use in said dialysis machines by dilution of said dialysis concentrate.

21. The container of claim 20 including greater than about 20 kg of said sodium chloride in particulate form.

22. The container of claim 21 including more than about 40 kg of said sodium chloride in particulate form.

23. The container of claim 20 wherein said first connecting means comprises male connecting means and said second connecting means comprises female connecting means.

24. A method for the central preparation and distribution of a dialysis concentrate to a plurality of dialysis machines comprising supplying a liquid stream comprising substantially only water to a central container including substantially only sodium chloride at least partially in solid form in an amount of at least about 10 kg therein, producing a substantially saturated solution of said sodium chloride in said central container, adding a separate substance to said substantially saturated sodium chloride solution to obtain said concentrate, and distributing said concentrate to a distribution conduit, said distribution conduit including a plurality of concentrate connectors for distribution of said concentrate thereto, whereby a dialysis fluid can be provided for use in said dialysis machines by dilution of said dialysis concentrate.

25. The method of claim 24 wherein said separate substance comprises acetic acid.

26. The method of claim 24 including preparing a medical treatment solution from said concentrate in each of said plurality of medical treatment devices.

27. The method of claim 26 wherein said medical treatment solution comprises a dialysis solution and said plurality of medical treatment devices comprises a plurality of dialyzers, and including diluting said concentrate and adding carbon dioxide gas to said concentrate prior to said distributing of said concentrate to said distribution conduit.

28. A method for the central preparation and distribution of a dialysis concentrate to a plurality of dialysis machines comprising supplying a liquid stream comprising substantially only water to a central container including substantially only sodium chloride at least partially in solid form therein, producing a substantially saturated solution of said sodium chloride in said central container, diluting said substantially saturated sodium chloride solution with water, adding carbon dioxide gas to said diluted sodium chloride solution to form said concentrate, and distributing said concentrate to a distribution conduit, said distribution conduit including a plurality of concentrate connectors for connection to said plurality of dialysis machines for distribution of said concentrate thereto, whereby said dialysis fluid may be provided for use in said dialysis machine by dilution of said dialysis concentrate.

29. The method of claim 28 including adding a separate substance to said concentrate.

30. The method of claim 29 wherein said separate substance comprises acetic acid.

31. Apparatus for the central preparation and distribution of a dialysis concentrate to a plurality of dialysis machines comprising central concentrate preparation means for preparing a substantially saturated solution from substantially only sodium chloride which is at least partially in solid form in an amount of at least about 10 kg and a supply of substantially only water, inlet means for supplying said water to said central concentrate preparation means, metering means for metering an additional substance into said substantially saturated sodium chloride solution to form said concentrate, and conduit means for supplying said concentrate to a distribution conduit for distribution to said plurality of dialysis machines, whereby a dialysis fluid can be provided for use in said dialysis machines by dilution of said dialysis concentrate.

32. The apparatus of claim 31 wherein said additional substance is selected from the group consisting of an acid and carbon dioxide.

33. The apparatus of claim 32 wherein said acid comprises acetic acid.

34. The apparatus of claim 31 wherein said central concentrate preparation means comprises at least one container for said sodium chloride at least partially in solid form.

35. The apparatus of claim 34 wherein said at least one container includes said sodium chloride in an amount of at least about 10 kg.

36. The apparatus of claim 35 wherein said at least one container includes said sodium chloride in an amount of greater than about 40 kg.

37. The apparatus of claim 34 wherein said central concentrate preparation means includes a water tank, and said inlet means includes a water supply conduit for supplying said water from said water tank to said at least one container, return conduit means for returning said concentrate to said central concentrate preparation means, and pump means for feeding said concentrate to said conduit means.

38. The apparatus of claim 37 including pressure means for measuring the pressure downstream of said at least one container and upstream of said pump means.

39. The apparatus of claim 38 including concentrate meter means for measuring the concentration of said sodium chloride in said concentrate upstream of said conduit means, and valve means for selectively diverting said concentrate for disposal based upon said concentration measured by said concentrate meter means.

40. Apparatus for the central preparation and distribution of a dialysis concentrate to a plurality of dialysis machines comprising central concentrate preparation means for preparing a substantially saturated solution from substantially only sodium chloride which is at least partially in solid form in an amount of at least about 10 kg and a supply of substantially only water, inlet means for supplying said water to said central concentrate preparation means, dilution means for diluting said substantially saturated solution of sodium chloride, metering means for metering an additional substance into said water or said substantially saturated sodium chloride solution to form said concentrate, and conduit means for supplying said concentrate to a distribution conduit for distribution to said plurality of dialysis machines, whereby a dialysis fluid can be provided for use in said dialysis machines by dilution of said dialysis concentrate.

41. The apparatus of claim 40 wherein said additional substance is selected from the group consisting of acid and carbon dioxide.

42. The apparatus of claim 41 wherein said additional substance comprises carbon dioxide.

43. A method for the central preparation and distribution of a dialysis concentrate to a plurality of dialysis machines comprising supplying a liquid stream comprising substantially only water to a central container including substantially only sodium chloride at least partially in solid form therein, producing a substantially saturated solution of said sodium chloride in said central container, adding a separate substance to said substantially saturated sodium chloride solution to obtain said concentrate, distributing said concentrate to a distribution conduit, diluting said concentrate and adding carbon dioxide gas to said concentrate prior to said distributing of said concentrate to said distribution conduit, said distribution conduit including a plurality of concentrate connectors for distribution of said concentrate thereto, and preparing a dialysis solution from said concentrate in each of said plurality of dialysis machines by dilution of said dialysis concentrate, said distribution conduit including a plurality of concentrate connectors for distribution of said concentrate thereto.

* * * * *

UNITED STATES PATENT AND TRADEMARK OFFICE
CERTIFICATE OF CORRECTION

PATENT NO. : 5,972,223
DATED : October 26, 1999
INVENTOR(S) : Jönsson *et al.*

It is certified that error appears in the above-identified patent and that said Letters Patent is hereby corrected as shown below:

Column 1, line 60, after "handled" insert --by the--.
Column 13, line 54, "others " should read --other,--.

Signed and Sealed this

First Day of August, 2000

Attest:

Q. TODD DICKINSON

*Attesting Officer*    *Director of Patents and Trademarks*